United States Patent [19]

Kao et al.

[11] Patent Number: 5,302,584
[45] Date of Patent: Apr. 12, 1994

[54] CARBAMATES OF RAPAMYCIN

[75] Inventors: Wenling Kao, Paoli; Magid A. Abou-Gharbia, Glen Mills, both of Pa.; Robert L. Vogel, Stratford, N.J.

[73] Assignee: American Home Products Corporation, Madison, N.J.

[21] Appl. No.: 54,655

[22] Filed: Apr. 23, 1993

Related U.S. Application Data

[63] Continuation-in-part of Ser. No. 960,597, Oct. 13, 1992, abandoned.

[51] Int. Cl.⁵ ............ C07D 491/06; A61K 31/675; A61K 31/395
[52] U.S. Cl. .................... 514/80; 514/291; 540/456
[58] Field of Search ............ 514/63, 291, 80; 540/452, 456

[56] References Cited

U.S. PATENT DOCUMENTS

| | | | |
|---|---|---|---|
| 3,929,992 | 12/1975 | Sehgal et al. | 340/546 |
| 3,993,749 | 11/1976 | Sehgal et al. | 540/546 |
| 4,316,885 | 2/1982 | Rakhit | 540/546 |
| 4,401,653 | 8/1983 | Eng | 540/546 |
| 4,650,803 | 3/1987 | Stella et al. | 540/546 |
| 4,885,171 | 12/1989 | Sehgal et al. | 540/546 |
| 5,078,999 | 1/1992 | Warner et al. | 540/546 |
| 5,080,899 | 1/1992 | Sturm et al. | 540/546 |
| 5,091,389 | 2/1992 | Ondeyka et al. | 540/546 |
| 5,100,883 | 3/1992 | Schiehser | 540/546 |
| 5,100,899 | 3/1992 | Calne | 540/546 |
| 5,118,677 | 6/1992 | Caufield | 540/546 |
| 5,118,678 | 6/1992 | Kao et al. | 540/546 |
| 5,130,307 | 7/1992 | Failli et al. | 540/546 |
| 5,194,447 | 3/1993 | Kao | 540/546 |

FOREIGN PATENT DOCUMENTS

| | | | |
|---|---|---|---|
| 0507555 | 10/1992 | European Pat. Off. | 540/546 |
| 9113899 | 9/1991 | PCT Int'l Appl. | 540/546 |

OTHER PUBLICATIONS

Kao, U.S. Patent Application Ser. No. 07/837,048, Feb. 18, 1992.
Vezina, C., J. Antibiot. 28, 721–726 (1975).
Sehgal, S. N., J. Antibiot. 28, 727–732 (1975).
Baker, H., J. Antibiot. 31, 539–545 (1978).
Martel, C., Can. J. Physiol. Pharmacol. 55, 48 (1977).
Staruch et al., FASEB 3,3441 (1989).
Dumont, F., FASEB 3, 5256 (1989).
Calne et al., Lancet, 1183–1185 (1978).
Morris, R., Med. Sci. Res. 17:877 (1989).
Baeder, W. L. Fifth Int. Conf. Inflamm. Res. Assoc. 121 (Abstract) (1990).
Meiser, B. M., J. Heart Lung Transplant 11 (pt 2): 197 (1992).
Kao, U.S. Patent Application Ser. No. 07/968,115, Oct. 29, 1992.

*Primary Examiner*—Robert T. Bond
*Attorney, Agent, or Firm*—Arnold S. Milowsky

[57] ABSTRACT

A compound of the structure

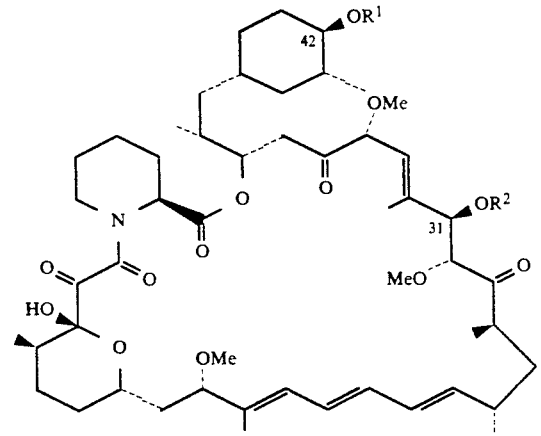

wherein
$R^1$ and $R^2$ are each, independently, hydrogen, $-CONH-[(CR^3R^4)_m(-A-(CR^5R^6)_n)_p]_q-B$;

(Abstract continued on next page.)

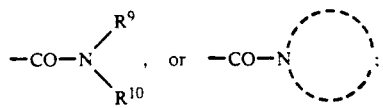

- $R^3$, $R^4$, $R^5$, $R^6$, and B are each, independently, hydrogen, alkyl, alkenyl, alkynyl, hydroxyalkyl, alkoxyalkyl, alkylthioalkyl, alkylaminoalkyl, dialkylaminoalkyl, arylalkyl, cycloalkyl, —$OR^7$, —$SR^7$, halogen, —CN, —$NO_2$, —$CF_3$, —$COR^7$, —$CO_2R^7$, —$CONHR^7$, —$SO_2R^7$, —$OSO_3R^7$, —$NR^7R^8$, —$NHCOR^7$, —$NHSO_2R^7$, or Ar;
- $R^7$ and $R^8$ are each, independently, hydrogen, alkyl, arylalkyl, alkenyl, alkynyl, hydroxyalkyl, alkoxyalkyl, alkylthioalkyl, alkylaminoalkyl, dialkylaminoalkyl, cycloalkyl;
- $R^9$ and $R^{10}$ are each, independently, alkyl, alkenyl, alkynyl, hydroxyalkyl, alkoxyalkyl, alkylthioalkyl, alkylaminoalkyl, dialkylaminoalkyl, arylalkyl, —$CF_3$, —$COR^7$, —$CO_2R^7$, —$CONHR^7$, —$SO_2R^7$, or Ar;
- A is —$CH_2$—, —$NR^7$—, —O—, —S—, —SO—, —$SO_2$—, —$PR^7$—, —CO—, —NHCO—, —NHSO—, or —$P(O)(R^7)$—;
- Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b]thiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted;

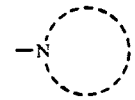

is a nitrogen containing heterocycle that may be saturated, unsaturated, or partially unsaturated, and may be optionally mono-, di-, or tri- substituted; with the proviso that $R^1$ and $R^2$ are not both hydrogen;
- m=0-6;
- n=0-6;
- p=0-1;
- q=0-1;
- or a pharmaceutically acceptable salt thereof which is useful as an immunosuppressive, antiinflammatory, antifungal, antiproliferative, and antitumor agent.

33 Claims, No Drawings

CARBAMATES OF RAPAMYCIN

CROSS-REFERENCE TO RELATED APPLICATIONS

This application is a continuation in part of Ser. No. 07/960,597, filed Oct. 13, 1992 is now abondoned.

BACKGROUND OF THE INVENTION

This invention relates to carbamates of rapamycin and a method for using them for inducing immunosuppression, and in the treatment of transplantation rejection, host vs. graft disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, antiinflammatory, antifungal, and antitumor agents.

DESCRIPTION OF THE INVENTION

This invention provides derivatives of rapamycin which are useful as immunosuppressive, antiinflammatory, antifungal, antiproliferative, and antitumor agents having the structure

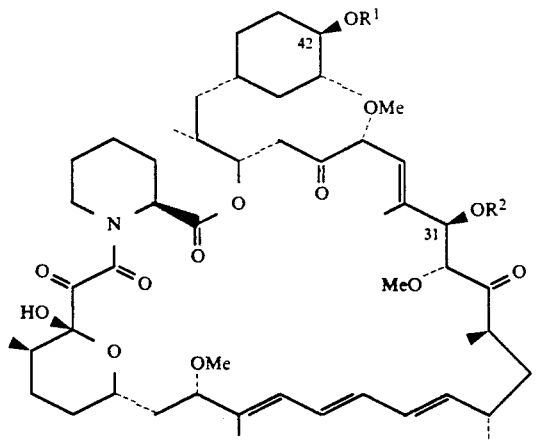

wherein
$R^1$ and $R^2$ are each, independently, hydrogen, $-CONH-[(CR^3R^4)_m(-A-(CR^5R^6)_n)_p]_q-B$;

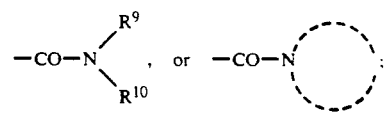

$R^3$, $R^4$, $R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-OR^7$, $-SR^7$, halogen, $-CN$, $-NO_2$, $-CF_3$, $-COR^7$, $-CO_2R^7$, $-CONHR^7$, $-SO_2R^7$, $-OSO_3R^7$, $-NR^7R^8$, $-NHCOR^7$, $-NHSO_2R^7$, or Ar;

$R^7$ and $R^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^9$ and $R^{10}$ are each, independently, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-CF_3$, $-COR^7$, $-CO_2R^7$, $-CONHR^7$, $-SO_2R^7$, or Ar;

A is $-CH_2-$, $-NR^7-$, $-O-$, $-S-$, $-SO-$, $-SO_2-$, $-PR^7-$, $-CO-$, $-NHCO-$, $-NHSO-$, or $-P(O)(R^7)-$;

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b]thiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H;

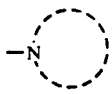

is a nitrogen containing heterocycle that may be saturated, unsaturated, or partially unsaturated, and may be optionally mono-, di-, or tri- substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H;

with the proviso that R$^1$ and R$^2$ are not both hydrogen;

m=0-6;
n=0-6;
p=0-1;
q=0-1;

or a pharmaceutically acceptable salt thereof.

The pharmaceutically acceptable salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the aryl portion of the arylalkyl substituent is a phenyl, piperazinyl, piperidinyl, or pyridyl group that is optionally mono-, di-, or tri- substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H.

It is preferred that

is a pyridyl, pyrazinyl, piperidinyl, morpholinyl, piperazinyl, pyrrolidinyl, thiazolyl, pyrimidinyl, isoxazolyl, pyrrolidinyl, or imidazolyl group that may be optionally substituted as described above.

Of these compounds, preferred members are those having the structure

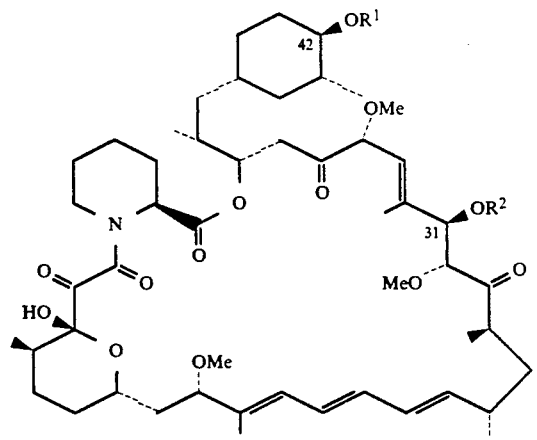

wherein
R$^1$ and R$^2$ are each, independently, hydrogen, or —CONH—[(CR$^3$R$^4$)$_m$(—A—(CR$^5$R$^6$)$_n$)$_p$]$_q$—B;
R$^3$, R$^4$, R$^5$, R$^6$, and B are each, independently, hydrogen, alkyl of 1-6 carbon atoms, arylalkyl of 7-10 carbon atoms, cycloalkyl of 3-8 carbon atoms, —OR$^7$, —SR$^7$, halogen, —CN, —NO$_2$, —CF$_3$, —COR$_7$, —CONH$_2$, —SO$_2$R$_7$, —OSO$_3$R$^7$, —NR$^7$R$^8$, —NHCOR$^7$, —NHSO$_2$R$^8$, or Ar;
A is —CH$_2$—, —NR$^7$—, —O—, —S—, —SO$_2$—, —PR$^7$—, or —P(O)(R$^7$)—;
R$^7$ and R$^8$ are each, independently, hydrogen, alkyl of 1-6 carbon atoms, arylalkyl of 7-10 carbon atoms, or Ar;
Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H;

with the proviso that R$^1$ and R$^2$ are not both hydrogen;

m=0-6;
n=0-6;
p=0-1;
q=0-1;

or a pharmaceutically acceptable salt thereof.

Preferred members also include those compounds in which R$^2$ is hydrogen; those in which p=0 and B is Ar; those in which p=0, B is Ar, and R$^2$ is hydrogen; those in which p=0, B is Ar, R$^2$ is hydrogen, and Ar is pyridyl, furyl, piperazinyl, piperazinyl, and piperidinyl; those in which m=0-3 and p=0; those in which m=2, n=0, p=1, q=1 and A is —O— or NR$^7$; those in which R$^1$ is

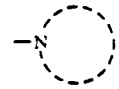

and R[2] is hydrogen; and those in which R[1] is

R[2] is hydrogen, and

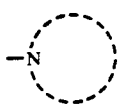

is an optionally substituted morpholinyl or piperazinyl group.

The compounds of this invention carbamylated at the 42-position or at both the 31- and 42-positions can be prepared by converting the 42- and/or 31-alcohols of rapamycin to a carbonate followed by reaction with an appropriately substituted amine to provide the desired carbamate. This scheme is illustrated below for the preparation of the compound of Example 2.

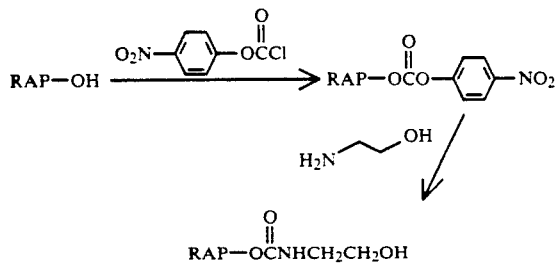

Alternatively the compounds of this invention carbamylated at the 42-position or at both the 31- and 42-positions can be prepared by reacting rapamycin with an appropriately substituted isocyanate under neutral conditions or in the presence of a base, such as pyridine. Preparation of carbamates of rapamycin using this method was disclosed in U.S. Pat. No. 5,118,678, which is hereby incorporated by reference.

The 31-carbamylated compounds of this invention can be prepared by protecting the 42-alcohol of rapamycin with a protecting group, such as with a tert-butyl dimethylsilyl group, followed by carbamylation of the 31-position by the procedures described above. Removal of the protecting group provides the 31-carbamylated compounds. In the case of the tert-butyl dimethylsilyl protecting group, deprotection can be accomplished under mildly acidic conditions.

Having the 31-position carbamylated and the 42-position deprotected, the 42-position can be carbamylated using a different amine (via the carbonate) or isocyanate than was reacted with the 31-alcohol, to give compounds having different carbamates at the 31- and 42-positions. Alternatively, the 42-carbamylated compounds, prepared as described above, can be reacted with a different amine (via the carbonate) or isocyanate to provide compounds having different carbamates at the 31- and 42-positions.

The amines and isocyanates used to prepare the compounds of the invention are commercially available or can be prepared by methods that are disclosed in the literature.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 42-oxorapamycin [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxy- and 15,27-bishydroxy-rapamycin [U.S. Pat. No. 5,102,876]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 2.2-9.9 nM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{{}^3\text{H-control thymus cells} - {}^3\text{H-rapamycin-treated thymus cells}}{{}^3\text{H-control thymus cells} - {}^3\text{H-test compound-treated cells}}$$

Representative compounds of this invention were also evaluated in an in vivo test procedure designed to determine the survival time of pinch skin graft from male BAB/c donors transplanted to male C₃H(H-2K) recipients. The method is adapted from Billingham R. E. and Medawar P. B., J. Exp. Biol. 28:385-402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. The following table shows the results that were obtained. Results are expressed as the mean survival time in days. Untreated (control) pinch skin grafts are usually rejected within 6-7 days. The results shown in Table 1 are based on a dose of 4 mg/kg of test compound. A survival time of 12.0±1.7 days was obtained for rapamycin at 4 mg/kg.

The following table summarizes the results of representative compounds of this invention in these two standard test procedures.

TABLE 1

EVALUATION OF IMMUNOSUPPRESSIVE ACTIVITY*

| Compound | LAF IC$_{50}$ (nM) | LAF (ratio) | Skin Graft (days ± SD) |
|---|---|---|---|
| Example 1 | 1.7 | 1.29 | 11.7 ± 0.5 |
| Example 2 | 1.8 | 1.22 | 10.3 ± 0.8 |
|  | 4.4 | 1.09 |  |
| Example 3 | 6.5 | 0.34 |  |
| Example 4 | 10.0 | 0.45 | 9.8 ± 0.8 |
| Example 5 | 2.1 | 1.19 |  |
| Example 6 | 0.8 | 5.1 | 11.40 ± 0.6 |
| Example 7 | 1.2 | 2.3 | 10.33 ± 0.5 |
| Example 8 | 0.2 | 4.4 |  |
| Example 10 | 0.1 | 3.8 | 10.17 ± 1.0 |
| Example 11 | 0.7 | 5.0 | 11.40 ± 0.9 |
| Example 12 | 1.1 | 3.8 | 9.80 ± 1.1 |
| Example 13 | 0.9 | 3.8 | 9.50 ± 0.6 |
| Example 14 | 0.5 | 3.8 | 9.17 ± 1.7 |
| Example 21 | 6.0 | 0.6 | 10.4 ± 0.5 |
| Example 23 | 3.4 | 1.4 |  |
| Example 24 | 40.0 | 0.1 |  |
| Example 26 | 0.2 | 6.2 |  |
| Example 27 | 1.2 | 1.2 |  |
| Example 28 | 4.2 | 1.1 |  |

*Calculation of the ratio was described supra.

The results of these standard pharmacological test procedures demonstrate immunosuppressive activity both in vitro and in vivo for the compounds of this invention. Positive ratios in the LAF test procedures indicates suppression of T-cell proliferation, thereby demonstrating the immunosuppressive activity of the compounds of this invention. As transplanted pinch skin grafts are typically rejected within 6-7 days without the use of an immunosuppressive agent, the increased survival time of the skin graft when treated with the compounds of this invention further demonstrates their utility as immunosuppressive agents.

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation, asthma, and eye uveitis.

Because the compounds of this invention are structurally similar to rapamycin and the carbamates of rapamycin disclosed in U.S. Pat. No. 5,118,678 and have a similar activity profile to rapamycin and the carbamates of U.S. Pat. No. 5,118,678, the compounds of this invention also are considered to have antitumor, antifungal activities, and antiproliferative activities. The compounds of this invention therefore are also useful in treating solid tumors, fungal infections, and hyperproliferative vascular diseases such as restenosis and atherosclerosis.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg-100 mg/kg, preferably between 0.001-25 mg/kg, and more preferably between 0.01-5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

Rapamycin 42-ester with carbamic acid

A solution of 2.0 g of rapamycin in 10 ml of dichloromethane and 2 mL of dry pyridine was cooled to −78° C. under a nitrogen atmosphere. To this solution, 662 mg 4-nitrophenyl chloroformate was added; the resulting solution was stirred at room temperature under nitrogen for 20 hours. The mixture was diluted with water and extracted with dichloromethane. The dichloromethane extract was washed with water, dried over MgSO$_4$ and evaporated. The residue was chromatographed on silica gel. Elution with 33% ethyl acetate in n-hexane gave 2.07 g of rapamycin 42-p-nitrophenyl carbonate as a white foam.

A solution of 630 mg rapamycin 42-p-nitrophenyl carbonate in 25 mL dichloromethane was treated at 0° with ammonia gas for one hour. The resulting yellow suspension was filtered and the filtrate was evaporated. The residue was chromatographed on silica gel. Elution with 25% n-hexane in ethyl acetate afforded 430 mg of the title compound as a white foam, mp 101°-103°.

IR(KBr): 3450 (OH and NH), 1720 (lactone and ketone C=O), 1645 (amide C=O), 1460, 1190, 890, 760 cm$^{-1}$. $^1$H NMR (CDCl$_3$, 400 MHz): δ4.6 (s, 2H, NH$_2$), 3.40, 3.33, 3.14 (all s, 3H, —OCH$_3$) ppm. MS (neg. ion FAB): 956 (M$^-$), 590, 364.

EXAMPLE 2

Rapamycin 42-ester with 2-hydroxyethyl carbamic acid

A solution of 270 mg rapamycin 42-p-nitrophenyl carbonate in 8 mL dichloromethane was treated at −10° C. under a nitrogen atmosphere with 61 mg ethanolamine in 0.5 mL dichloromethane. The yellow solution was stirred at 0° C. under a nitrogen atmosphere for 45 minutes. The reaction mixture was diluted with 120 mL dichloromethane, washed with 1N HCl, water, dried with MgSO$_4$ and evaporated. The residue was chromatographed on silica gel. Elution with ethyl acetate/n-hexane (2/1) afforded 85 mg of the title compound as a white foam, mp 100°-105°.

IR(KBr): 3430 (OH, NH), 1720 (lactone and ketone C=O), 1640 (amide C=O), 1520, 1450, 1240, 1080, 985 and 760 cm$^{-1}$. $^1$H NMR (CDCl$_3$, 400 MHz): 3.70 (m, 2H, —CH$_2$—OH), 3.65 (m, 2H, —NH—CH$_2$), 3.38, 3.33, 3.14 (all s, 3H, —OCH$_3$) ppm. MS (neg ion FAB): 1000 (M$^-$), 590, 408, 297.

The following representative compounds can be prepared from rapamycin 42-p-nitrophenyl carbonate (prepared as disclosed in Example 1) and the appropriate amine by employing the method used to prepare the title compound in Example 2.

Rapamycin 42-ester with cyclohexyl carbamic acid
Rapamycin 42-ester with napthyl carbamic acid
Rapamycin 42-ester with 1-(2-naphthylethyl) carbamic acid
Rapamycin 42-ester with 3-cyanopropyl carbamic acid
Rapamycin 42-ester with 2-hydroxy-hexafluoroisopropyl carbamic acid
Rapamycin 42-ester with 2-methoxycarbonyl-2-(4-hydroxyphenyl)ethyl carbamic acid
Rapamycin 42-ester with 1-(2-hydroxyisoxazolyl)-methyl carbamic acid
Rapamycin 42-ester with 2-methoxyisopropyl carbamic acid
Rapamycin 42-ester with 2,2-dimethoxyethyl carbamic acid
Rapamycin 42-ester with 2-phosphonoxyethyl carbamic acid
Rapamycin 42-ester with 2-sulfinoethyl carbamic acid
Rapamycin 42-ester with 2-methoxyethyl carbamic acid
Rapamycin 42-ester with 1-carboxy-3-(methylsulfinyl)-propyl carbamic acid
Rapamycin 42-ester with 1-methoxycarbonyl-3-(methylthio)propyl carbamic acid
Rapamycin 42-ester with 1,3-(bis-ethoxycarbonyl)propyl carbamic acid Rapamycin 42-ester with 1-ethoxycarbonyl-2-methylpropyl carbamic acid
Rapamycin 42-ester with 1-butoxycarbonyl-2-hydroxyethyl carbamic acid
Rapamycin 42-ester with 1-methoxycarbonyl-2-(4-hydroxyphenyl)ethyl carbamic acid
Rapamycin 42-ester with 1-methoxycarbonyl-2-(5-imidazolyl)ethyl carbamic acid
Rapamycin 42-ester with 1-(phenoxycarbonyl)methyl carbamic acid
Rapamycin 42-ester with 1-carboxy-2-methyl-2-phosphonoxyethyl carbamic acid
Rapamycin 42-ester with 1-carbophenylmethoxy-2-(phenylmethoxy)ethyl carbamic acid
Rapamycin 42-ester with 1-(4-bromopehnoxymethyl)ethyl carbamic acid
Rapamycin 42-ester with 2-(phenylcarbonyloxy)ethyl carbamic acid
Rapamycin 42-ester with 1-propylcarbonyloxy-3-methylpropyl carbamic acid
Rapamycin 42-ester with 1-phenylmethoxycarbonyl-3-(3-indolyl)propyl carbamic acid
Rapamycin 42-ester with 1-propyloxycarbonyl-3-(methylsulfinyl)propyl carbamic acid
Rapamycin 42-ester with 1-(butyloxycarbonyl)-3-(methylthio)propyl carbamic acid
Rapamycin 42-ester with 1-((4-chlorophenyl)methoxycarbonyl)-2-(phenylmethylthio)ethyl carbamic acid
Rapamycin 42-ester with 1-methoxycarbonyl-1-(trifluoromethyl)methyl carbamic acid
Rapamycin 42-ester with 1-(2-methylpropoxycarbonyl)-2-chloroethyl carbamic acid
Rapamycin 42-ester with 1-ethoxycarbonyl-3-(aminocarbonyl)propyl carbamic acid
Rapamycin 42-ester with 1-methoxycarbonyl-2-(P-(2,3-dihydroxypropyloxy)phosphonoxy)ethyl carbamic acid
Rapamycin 42-ester with 1-cyano-1-(ethoxycarbonyl)methyl carbamic acid
Rapamycin 42-ester with 1-methoxycarbonyl-2-(carboxymethylthio)ethyl carbamic acid
Rapamycin 42-ester with 1-phenoxycarbonyl-1-(2-thenyl)methyl carbamic acid
Rapamycin 42-ester with 1-phenylmethoxycarbonyl-2-(sulfo)ethyl carbamic acid
Rapamycin 42-ester with 4-(ethylthio)butylamine
Rapamycin 42-ester with 2-phenylthioethyl carbamic acid
Rapamycin 42-ester with 2-sulfothioethyl carbamic acid
Rapamycin 42-ester with 2-thioethyl carbamic acid
Rapamycin 42-ester with 2-benzoylthioethyl carbamic acid
Rapamycin 42-ester with 2-phosphonothioethyl carbamic acid
Rapamycin 42-ester with 2-(methylthio)propyl carbamic acid
Rapamycin 42-ester with 1-ethoxycarbonyl-2-sulfinoethyl carbamic acid
Rapamycin 42-ester with 2-(2-chloro-6-fluorophenylmethylthio)ethyl carbamic acid
Rapamycin 42-ester with N-(2-imidazolyl)amino carbamic acid
Rapamycin 42-ester with 2-(N,N-dipropylamino)ethyl carbamic acid
Rapamycin 42-ester with 2-(N,N-bis-(2-hydroxyethyl)amino)ethyl carbamic acid
Rapamycin 42-ester with 2-(N-phenylmethyl-N-((3-ethyl-5-methyl)-4-isoxazolylmethyl)ethyl carbamic acid
Rapamycin 42-ester with 1-((N-methyl-N-carboxymethyl)amino)carbonylmethyl carbamic acid
Rapamycin 42-ester with cyanomethyl carbamic acid
Rapamycin 42-ester with 1-phenyl-1-cyanomethyl carbamic acid
Rapamycin 42-ester with 1-chloro-1-(phenylsulfonyl)methyl carbamic acid
Rapamycin 42-ester with 1-isoquinolyl carbamic acid
Rapamycin 42-ester with 1-(4-chlorophenyl)-1-(2-(1,2,3,4-tetrahydroisoquinolyl))methyl carbamic acid

EXAMPLE 3

Rapamycin 42-ester with 2-(dimethylamino)ethyl carbamic acid

A solution of 100 mg rapamycin 42-p-nitrophenyl carbonate in 2 mL dichloromethane was treated at 0° C. under a nitrogen atmosphere with 44 mg N,N-dimethylethylenediamine in 0.5 mL dichloromethane. The reaction mixture was stirred at 0° C. under nitrogen for 0.5 hour. The reaction mixture was diluted with dichloromethane, washed with water, and dried over $MgSO_4$. After filtration, the dichloromethane solution was cooled to 0° C. under a nitrogen atmosphere and treated with 1.5 ml of 0.1N HCl solution in ether. The crystalline material was collected by filtration, washed with ether and dried at 56° under vacuum to afford 80 mg of the title compound as a white solid which was isolated as the hydrochloride dihydrate, mp 125°–130° (decomposition).

IR(KBr): 3400 (OH and NH), 1720 (lactone and ketone C=O), 1640 (amide C=O), 1450, 1240, 1090, and 980 $cm^{-1}$. NMR (DMSO-$D_6$, 400 MHz) $\delta 7.36$ (1H, —OC(O)NH), 3.34 (m, 2H,—NHCH$_2$), 3.10 (m, 2H, CH$_2$—N$^+$H(CH$_3$)$_2$), 3.26, 3.14, 3.04 (all s, 3H, —OCH$_3$), 2.76 (s, 6H —N$^+$H(CH$_3$)$_2$) ppm. MS (neg. ion FAB): 1027 (M$^-$), 590, 435, 167.

Analysis Calcd. for $C_{56}H_{89}N_3O_{14} \cdot HCl \cdot 2\ H_2O$: C, 61.09; H, 8.60; N, 3.81. Found: C, 61.06; H, 8.55; N, 3.91.

EXAMPLE 4

Rapamycin 42-ester with aminocarbamic acid

A solution of 108 mg rapamycin 42-p-nitrophenyl carbonate in 5 mL dichloromethane, cooled to −10° C. under a nitrogen atmosphere, was treated with 6.4 mg hydrazine in 0.4 mL dichloromethane. The reaction mixture was stirred at −10° C. under nitrogen for five hours. The yellow suspension was filtered, the filtrate evaporated, and the yellow residue was chromatographed on silica gel. Elution with ethyl acetate/n-hexane (4/1) afforded 52 mg of the title compound as a white solid, mp 110°–115°.

IR(KBr): 3400 (OH and NH), 1720 (lactone and ketone C=O)), 1640 (amide C=O), 1450, 1090 and 750 $cm^{-1}$. $^1$H NMR (CDCl$_3$, 400 MHz): $\delta 3.37$, 3.34, 3.14 (all s, 3H, —OCH$_3$) ppm. MS (neg ion FAB): 971 (M$^-$), 590,167.

EXAMPLE 5

Rapamycin 42-ester with hydroxycarbamic acid

A solution of 210 mg hydroxylamine hydrochloride in 3 ml 1N KOH aqueous solution was diluted with 3 mL tetrahydrofuran. The solution was stirred at −78° C. under nitrogen and 110 mg of rapamycin 42-p- nitrophenyl carbonate was added. The resulting mixture was stirred at 0° C. under nitrogen for 3 hours, diluted with water, and extracted with ethyl acetate. The extract was washed with brine, dried with MgSO4, and evaporated. The residue was chromatographed on silica gel. Elution with ethyl acetate/n-hexane (2/1) afforded 20 mg of the title compound as a foam, mp 107°-110°.

IR(KBr): 3400 (OH and NH), 1740 (lactone C=0), 1720 (ketone C=0), 1640 (amide C=0), 1450, 1100, 985, 750 cm$^{-1}$. $^1$H NMR (CDCl3, 400 MHz): δ3.37, 3.35, 3.14 (all s, 3H, —OCH3) ppm. MS (neg ion FAB): 972 (M$^-$), 913, 950.

EXAMPLE 6

Rapamycin 42-ester with 2-(pyridin-2-yl)-ethyl carbamic acid

A solution of 210 mg rapamycin 42-p-nitrophenyl carbonate in 8 ml dichloromethane was treated at $-10°$ under N2 with 122 mg 2-(2-amino-ethyl)-pyridine in 1 ml dichloromethane. The reaction mixture was stirred at 0° under N2 for one hour, diluted with 200 ml dichloromethane, washed with ice-cold 1N HCl, water, and dried with MgSO4. The solvent was evaporated and the residue chromatographed on silica gel. Elution with ethyl acetate/n-hexane (4/1) afforded 70 mg of the title product as a white solid, mp 95°-98°.

IR (KBr): 3400 (OH and NH), 1720 (lactone and ketone C=0), 1645 (amide C=0), 1450, 1250, 1090, 1100 and 990 cm$^{-1}$.

$^1$H NMR (CDCl3, 400 MHz): δ8.52 (d, J=12 cps, 1H, proton c), 7.59 (t, 1H, proton b), 7.12 (m, 2H, protons a), 3.32, 3.31 and 3.12 (each s, 3H, OCH3), 3.58 (t, 2H, protons e), 2.97 (t, 2H, protons d) ppm. MS (neg. ion FAB): 1061 (M$^-$), 590, 469.

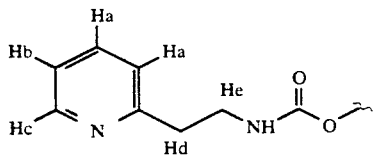

EXAMPLE 7

Rapamycin 42-ester with 2-(pyridin-2-yl)-ethyl carbamic acid hydrochloride salt

A solution of 330 mg rapamycin 42 ester with 2-(pyridin-2-yl)-ethyl carbamic acid in a mixture of one ml ethyl acetate and 4 ml ether was treated at $-78°$ under N2 with 0.5 ml 1N HCl (gas) in ether. The hydrochloride salt formed instantly. Stirring was continued at $-78°$ under N2 for ¼ hour. The product was collected by filtration, washed with ether, and dried in vacuum to afford 198 mg of the title product as a white solid, mp 102°-110°(dec).

IR (KBr): 3400 (OH, NH), 1720 (lactone and ketone C=0), 1640 (amide C=0), 1520, 1450, 1150, 1100, 990 cm$^{-1}$.

$^1$H NMR (DMSO-D6, 400 MHz): δ8.77 (d, J=12 cps, 1H, proton c), 8.40 (t, 1H, proton b), 7.83 (m, 2H, protons a), 3.63 (t, 2H, protons 3, 3.00 (t, 2H, protons d), 3.43, 3.29, 3.03 (each s, 3H, —OCH3) ppm. MS (neg ion FAB): 1061 (M$^-$), 590, 469.

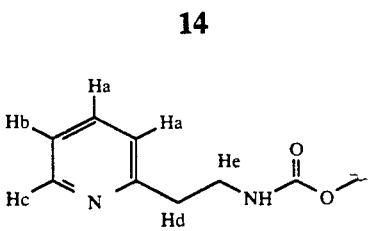

EXAMPLE 8

Rapamycin 42-ester with 2-(pyridin-2-yl)ethylcarbamic acid methanesulfonate salt A solution of 16 mg (0.16 mmole) methanesulfonic acid in 1 mL ether was added to a solution of 160 mg (0.15 mmole) rapamycin 42-ester with 2-(pyridin-2-yl)ethylcarbamic acid in 2 mL ethyl acetate and 4 mL ether at $-78°$ C. under nitrogen. After warming to 20°, the solvent was decanted and the residue was triturated thrice with ether, leaving 108 mg title compound as a pale yellow solid, mp 95°-110° C. (dec).

IR (KBr): 3520, 2950, 1725, 1650, 1460, and 778 cm$^{-1}$.

$^1$H NMR (CDCl3, 400 MHz): δ8.74 (d, 1H, 6-pyridyl); 3.35 (s, 3H, OMe); 3.34 (s, 3H, OMe); 3.14 (s, 3H, OMe); 2.92 (s, 3H, methanesulfonate) ppm. MS (neg ion FAB): 1061 (M$-$), 590.

EXAMPLE 9

Rapamycin 42-ester with 2-(pyridin-2-yl)ethylcarbamic acid maleate salt

A solution of 21 mg (0.18 mmole) maleic acid in 1.0 mL ether was added to a solution of 185 mg (0.17 mmole) rapamycin 42-ester with 2-(pyridin-2-yl)ethylcarbamic acid in 3 mL ethyl acetate and 2 mL ether at $-78°$ C. under nitrogen. After warming to 15°, the mixture was diluted with ether, the solvent was decanted and the residue was triturated with ether. Filtration, followed by diluting the filtrate with hexane and refiltration yielded the title compound as a white solid, mp 101°-117° C.

IR (KBr): 3430, 2950, 1725, 1645, 1460, and 870 cm$^{-1}$.

$^1$H NMR (CDCl3, 400 MHz): δ8.76 (d, 1H, 6-pyridyl); 6.40 (s, 2H, maleic acid vinyl); 3.35 (s, 3H, OMe); 3.34 (s, 3H, OMe); 3.15 (s, 3H, OMe) ppm. MS (neg ion FAB): 1061 (M$-$), 590.

EXAMPLE 10

Rapamycin 42-ester with 2-pyridinylmethyl carbamic acid

A solution of 1.05 g rapamycin 42-p-nitrophenyl carbonate in 20 ml dichloromethane was treated at $-10°$ under N2 with 620 mg 2-aminomethylpyridine in 1 ml dicholormethane. The reaction mixture was stirred at 0° under N2 for 3 hours, diluted with 180 ml dichloromethane, washed with saturated NaHCO3 (3×30 ml) and dried with MgSO4. The solvent was evaporated and the residue chromatographed on silica gel. Elution with ethyl acetate/n-hexane (4/1) afforded 560 mg of the title product as a white solid, mp 94°-97°.

IR(KBr): 3420 (OH, NH), 1720 (lactone and ketone C=0), 1645 (amide C=0), 1520, 1450, 1250, 1100, 990 cm$^{-1}$.

$^1$H NMR (CDCl3, 400 MHz): δ8.53 (d, J=12 cps, 1H, proton d), 7.65 (m, 1H, proton c), 7.27 (d, J=12 cps, 1H, proton a), 7.17 (m, 1H, proton b), 5.72 (m, 1H, —NH), 4.49 (d, J=10 cps, 2H, protons e), 3.37, 3.32, 3.13 (each s, 3H, —OCH₃) ppm. MS (neg. ion FAB): 1047 (M⁻), 590, 455.

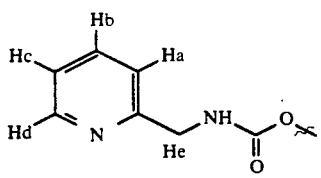

EXAMPLE 11

Rapamycin 42-ester with 2-pyridinylmethyl carbamic acid hydrochloride salt

A solution of 305 mg rapamycin 42-ester with 2-pyridinylmethyl carbamic acid in a mixture of one ml ethyl acetate and 4 ml ether was treated at −78° under N₂ with 0.55 ml 1N HCl solution. Crystalline material formed immediately. The reaction mixture was stirred at −78° under N₂ for ½ hr, the solid material was collected by filtration, washed with ether and dried in vacuo to give 270 mg of the title product as a white solid, mp 109°-113°(dec).

IR (KBr): 3430 (OH, NH), 1740 (lactone, ketone C=O), 1645 (amide C=O), 1520, 1455, 1250, 1100, 995 cm⁻¹.

¹H NMR (DMSO-D₆): δ8.70 (d, J=12 cps, 1H, proton d), 8.28 (t, 1H, proton c), 7.91 (t, 1H, proton b), 7.69 (t, 1H, proton b), 7.65 (d, 1H, proton a), 4.39 (d, 2H, protons e), 3.28, 3.14, 3.05 (each s, 3H, —OCH₃) ppm. MS (neg ion FAB): 1061 (M⁻), 590, 469.

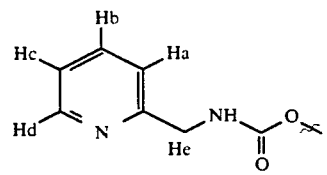

EXAMPLE 12

Rapamycin 42-ester with 3-pyridinylmethyl carbamic acid

The title compound was prepared according to the procedure in Example 6. mp 109°-111°

IR (KBr): 3400 (OH, NH), 1720 (lactone, ketone C=O), 1645 (amide C=O), 1450, 1250, 1100, 990 cm⁻¹.

¹H NMR (CDCl₃, 400 MHz): δ8.53 (m, 2H, proton c), 7.65 (m, 1H, proton b), 7.26 (m, 1H, proton a), 4.39 (d, J=12 cps, 2H, protons e), 3.36 (m), 3.32 (s), 3.12 (s) (all 3H, —OCH₃) ppm.

MS (neg ion FAB): 1047 (M⁻), 590.

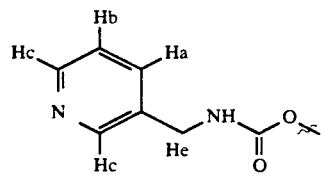

EXAMPLE 13

Rapamycin 42-ester with 3-pyridinylmethyl carbamic acid hydrochloride salt

The title compound was prepared according to the procedure in Example 7.

mp 106°-110° (dec)

IR (KBr): 3400 (OH, NH), 1720 (lactone, ketone C=O), 1645 (amide C=O), 1460, 1250, 1110, 990 cm⁻¹.

¹H NMR (DMSO-D₆, 400 MHz): δ8.71 (m, 2H, protons c), 8.25 (d, J=12 cps, 1H, proton a), 7.91 (m, 1H, proton b), 4.34 (d, 2H, protons e), 3.26, 3.14, 3.04 (each s, 3H, —OCH₃) ppm. MS (neg ion FAB): 1047 (M⁻), 590.

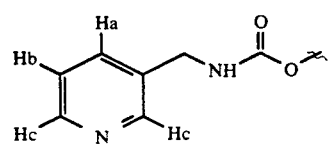

EXAMPLE 14

Rapamycin 42-ester with 4-pyridinylmethyl carbamic acid

The title compound was prepared according to the procedure in Example 6.

mp 109°-113°

IR (KBr): 3400 (OH, NH), 1720 (lactone, ketone C=O), 1645 (amide C=O), 1520, 1450, 1250, 1100, 990 cm⁻¹.

¹H NMR (CDCl₃, 400 MHz): δ8.56 (d, J=12 cps, 2H, protons b), 7.24 (d, J=12 cps, 2H, protons a), 4.40 (d, J=13 cps, 2H, protons c), 3.38, 3.33, 3.14 (each s, 3H, —OCH₃) ppm. MS (neg ion FAB): 1047 (M⁻) 590.

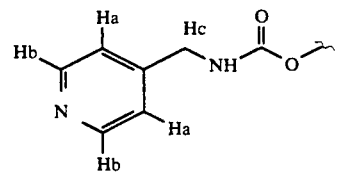

EXAMPLE 15

Rapamycin 42-ester with 4-pyridinylmethyl carbamic acid hydrochloride salt

The title compound was prepared according to the procedure in Example 7.

mp 109°-114°

IR (KBr): 3400 (OH, NH), 1720 (lactone, ketone C=O), 1645 (amide C=O), 1510, 1455, 1250, 1100, 990 cm⁻¹.

¹H NMR (DMSO-D₆): δ8.81 (d, J=13 cps, 2H, protons b), 7.81 (d, J=13 cps, 2H, protons a), 4.43 (d, J=12 cps, 2H, protons e), 3.30, 3.14, 3.04 (each s, 3H, —OCH₃) ppm. MS (neg ion FAB): 1047 (M⁻), 590.

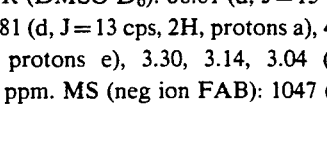

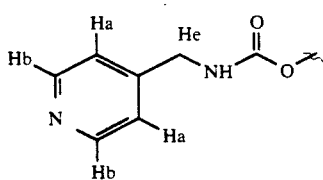

EXAMPLE 16

Rapamycin 42-ester with 2-furylmethyl carbamic acid

The title compound was prepared according to the procedure in Example 6.

mp 103°–105°

IR (KBr): 3400 (OH, NH), 1720 (lactone, ketone C=O), 1645 (amide C=O), 1520, 1460, 1250, 1100, 990 cm$^{-1}$.

$^1$H NMR (CDCl$_3$, 400 MHz): δ7.35 (d, 1H, proton b), 6.32 (m, 1H, proton a), 6.24 (d, 1H, proton c), 4.36 (d, J=13 cps, 2H, protons e), 3.36, 3.33, 3.14 (each s, 3H, —OCH$_3$) ppm. MS (neg. ion FAB): 1036 (M$^-$), 590.

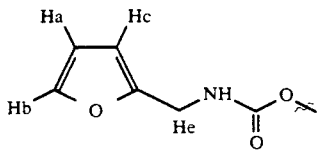

EXAMPLE 17

Rapamycin 42-ester with 2-pyridinylmethyl carbamic acid methanesulfonate salt

The title compound was prepared from the compound of Example 10 and methane sulfonic acid, and was isolated as a trihydrate.

mp 92°–95°

IR (KBr): 3400 (OH, NH), 1720 (lactone, ketone C=O), 1640 (amide C=O), 1520, 1450, 1450, 1240–1160 (sulfonate), 1100, 1040 (sulfonate), 990 cm$^{-1}$.

$^1$H NMR (DMSO-D$_6$): δ8.72 (d, J=13 cps, 1H, proton e), 8.31 (t, 1H, proton c), 7.93 (t, 1H, —NH), 7.73 (t, 1H, proton b), 7.69 (d, J=15 cps, 1H, proton a), 4.44 (d, J=10) cps, 2H, protons f), 3.29, 3.14, 3.04 (each s, 3H, —OCH$_3$), 2.31 (s, 3H,

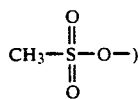

ppm

C/H/N analysis for C$_{59}$H$_{29}$N$_3$O$_{17}$S$_1$•3 H$_2$O: Calc: 59.12/7.99/3.50; Found: 59.48/7.95/3.41.

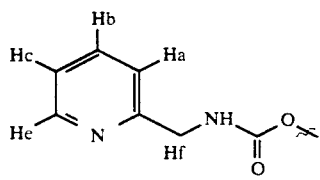

EXAMPLE 18

Rapamycin 42-ester with 4-hydroxybutyl carbamic acid

A solution of 600 mg rapamycin 42-p-nitrophenyl carbonate in 7.5 ml dichloromethane was treated at 0° under N$_2$ with 300 mg 4-amino-butanol in 0.5 ml dichloromethane. The yellow solution was stirred at 0° under N$_2$ for 2 hours. The mixture was diluted with 120 ml dicholoromethane, washed with 1N HCl, water, and dried with MgSO$_4$. The solvent was evaporated and the residue chromatographed on silica gel. Elution with ethyl acetate/n-hexane (2/1) afforded 245 mg of the title product as a solid, mp 105°–108°.

IR (KBr): 3420 (OH and NH), 1720 (lactone and ketone C=O), 1650 (amide C=O), 1530, 1455, 1250, 1110 and 990 cm$^{-1}$.

$^1$H NMR (CDCl$_3$, 400 MHz): δ3.65 (t, 2H, —CH$_2$OH), 3.2 (m, 2H, —NHCH$_2$—), 3.37, 3.33 and 3.14 (all s, 3H each, —OCH$_3$) ppm. MS (neg ion FAB): 1028 (M$^-$), 996, 590, 436, 167.

EXAMPLE 19

Rapamycin 42-ester with (S)-1-methyl-2-hydroxyethyl carbamic acid

A solution of 600 mg rapamycin 42-p-nitrophenyl carbonate in 7.5 ml dichloromethane was treated at 0° under N$_2$ with 500 mg (S)-(+)-2-amino-1-propanol in 0.5 ml dichloromethane. The yellow solution was stirred at 0° under N$_2$ for 2 hours. The mixture was diluted with 200 ml dichloromethane, washed with 1N HCl, water, and dried with MgSO$_4$. The solvent was evaporated and the residue chromatographed on silica gel. Elution with ethyl acetate/n-hexane (3/1) afforded 156 mg of the title product as a white solid, mp 99°–103°.

IR (KBr): 3440 (OH and NH), 1720 (lactone and ketone C=O), 1650 (amide C=O), 1520, 1455, 1110 and 995 cm$^{-1}$.

$^1$H NMR (CDCl$_3$, 400 MHz): 3.70 (m, 2H, —CH$_2$OH), 3.38, 3.20, and 3.16 (all s, 3H each, —OCH$_3$), 1.15 (d, 3H,

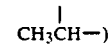

ppm. MS (ng. ion FAB): 1014 (M−), 983, 590 422, 167.

EXAMPLE 20

Rapamycin 42-ester with (R)-1-methyl-2-hydroxyethyl carbamic acid

A solution of 600 mg rapamycin 42-p-nitrophenyl carbonate in 7.5 ml dichloromethane was treated at 0° under N$_2$ with 600 mg (R)-(−)-2-amino-1-propanol in 0.5 ml dichloromethane. The yellow solution was stirred at 0° under N$_2$ for 2 hours. The mixture was diluted with 200 ml dichloromethane, washed with a saturated NaHCO$_3$ aqueous solution, 1N HCl solution, and dried with MgSO$_4$. The solvent was evaporated and the residue chromatographed on silica gel. Elution with ethyl acetate/n-hexane (3/1) afforded 260 mg of the title product as a white solid, mp 102°–106°.

IR (KBr): 3440 (OH and NH), 1720 (lactone and ketone C=O), 1650 (amide C=O), 1520, 1460, 1110 and 1000 cm$^{-1}$.

¹H NMR (CDCl₃, 400 MHz): δ3.70 (m, 2H, —CH₂OH). 3.37, 3.33 and 3.14 (all s, 3H, —OCH₃), 1.17 (d, 3H,

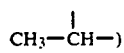

ppm. MS (neg. ion FAB): 1014 (M⁻), 893, 590.

EXAMPLE 21

Rapamycin 42-ester with 2-(2-aminoethoxy)ethyl carbamic acid

A solution of 600 mg rapamycin 42-p-nitrophenyl carbonate in 7.5 ml dichloromethane was treated at 0° under N₂ with 500 mg 2-(2-aminoethoxy)ethanol in 0.5 ml dichloromethane. The yellow solution was stirred at 0° under N₂ for 1.5 hours. The mixture was diluted with 150 ml dichloromethane, washed with a saturated NaHCO₃ aqueous solution, 1N HCl solution, and dried with MgSO₄. The solvent was evaporated and the residue chromatographed on silica gel. Elution with ethyl acetate/n-hexane (3/1) afforded 265 mg of the title product as a white solid, mp 100°-102°.

IR (KBr): 3430 (OH and NH), 1720 (lactone and ketone C=O), 1650, 1520, 1455, 1110, 1020 and 990 cm⁻¹.

¹H NMR (CDCl₃, 400 MHz): δ3.74 (t, 2H, —CH₂OH), 3.58 (m, 6H, —CH₂OCH₂CH₂—O—), 3.38, 3.33 and 3.14 (all s, 3H each, —OCH3) ppm. MS (neg ion FAB): 1044 (M⁻), 590, 452, 167.

EXAMPLE 22

Rapamycin 42-ester with 4-(2-hydroxyethyl)piperazine-1-carboxylic acid

A solution of 1-(2-hydroxyethyl)piperazine) (130 mg, 1.0 mmole) in 1 mL dry dichloromethane was added to a solution of 330 mg rapamycin 42-p-nitrophenyl)carbonate (0.31 mmole) in 6 mL dry dichloromethane at −8° under nitrogen and stirred at −8° for 1.5 hours. The reaction mixture was partitioned between dichloromethane and water/brine, the aqueous portion was extracted with dichloromethane, the combined organic portion was washed with brine, dried over MgSO₄ and evaporated to a white solid foam. Flash chromatography through silica gel using 2% methanol in dichloromethane yielded 140 mg of the title compound as a white solid, mp 112°-120° C.

IR (KBr): 3450, 2950, 1725, 1650, 1460, 1250 and 995 cm⁻¹.

NMR (CDCl₃, 400 MHz): δ3.64 (t (J=5.2 Hz), 2H, H_d); 3.51 (broad, 4H, H_a); 3.39 (s, 3H, OMe); 3.33 (s, 3H, OMe); 3.14 (s, 3H, OMe); 2.57 (t (J=5.2 Hz), 2H, H_c); 2.49 (broad, 4H, H_b) ppm. MS (neg. ion FAB): m/z at 1069 (m⁻), 590.

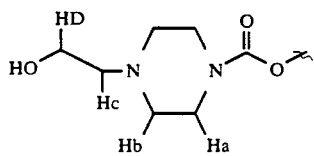

EXAMPLE 23

Rapamycin 42-ester with 4-(3-hydroxypropyl)piperazine-1-carboxylic acid

A solution of 130 mg (0.90 mmole) of 1-(3-hydroxypropyl)piperazine in 2 mL dichloromethane was added to a solution of 320 mg (0.30 mmole) rapamycin-42-(4-nitrophenyl)carbonate in 6 mL dichloromethane under nitrogen at −5° C. and allowed to warm to 20° with stirring. After 4 hours, the reaction mixture was partitioned between dichloromethane and water/brine. The organic portion was washed with brine and flash chromatographed through silica gel using methanol (2.0 to 3.0%) in dichloromethane, yielding 115 mg product as a white solid, mp 104°-113° C.

IR (KBr): 3430, 2930, 1715, 1640, 1450, 1240, and 985 cm⁻¹.

NMR (CDCl3, 400 MHz): δ3.81(t (J=5.2 Hz), 2H, Hd); 3.49 (broad, 4H, Ha); 3.38 (s, 3H, OMe); 3.33 (s, 3H, OMe); 3.13 (s, 3H, OMe); 2.62 (t (J=5.4 Hz), 2H, Hc); 2.48 (broad, 4H, Hb) ppm.

MS (neg ion FAB): 1083 (M⁻), 590.

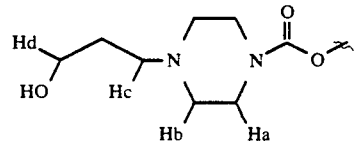

EXAMPLE 24

Rapamycin 42-ester with [3-[bis(2-hydroxyethyl)amino]propyl]carbamic acid

A solution of 130 mg (0.80 mmole) of N-(3-aminopropyl)diethanolamine in 2 mL dichloromethane was added to a solution of 330 mg (0.31 mmole) rapamycin-42-(4-nitrophenyl)carbonate in 8 mL dichloromethane under nitrogen at 0° C. and stirred at that temperature for one hour. The reaction mixture was partitioned between dichloromethane and brine. The organic portion was washed with brine and flash chromatographed through silica gel using 5% methanol in dichloromethane to yield 150 mg product as a white solid, mp 93°-107° C. IR (KBr): 3420, 2935, 1715, 1640, 1450 and 985 cm⁻¹.

NMR (CDCl3, 400 MHz): δ5.69 (broad, 1H, Hj); 3.67 (mult, 6H, He and Hh); 3.36 (s, 3H, OMe); 3.33(s, 3H, OMe); 3.14 (s, 3H, OMe); 2.68 (mult, 6H, Hf and Hg) ppm.

MS (neg ion FAB): 1101 (M⁻), 590.

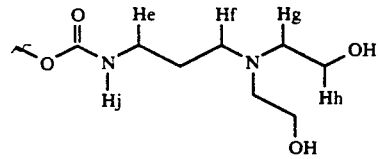

EXAMPLE 25

Rapamycin 42-ester with dihydroxyispropyl carbamic acid

To a 600 mg serinol in 3 ml methanol solution at −10° under N₂, was added 250 mg rapamycin 42-p-nitrophenyl carbonate in 1 ml chloroform. The resulting solution was stirred at −10° under N₂ for 2 hours, diluted with 120 ml chloroform, washed with water (3×20 ml), and dried with MgSO₄. The solvent was evaporated and the residue chromatographed on silica gel. Elution with ethyl acetate/n-hexane (4/1) afforded 90 mg the title product as a solid, mp 108°-113°.

IR (KBr): 3450 (OH and NH), 1730 (ketone and lactone), 1655 (amide C=O), 1520, 1460, 1250, 1100, 1000 CM⁻¹.

¹H NMR (CDCl₃, 400 MHz): δ4.69 (m, 1H, C-42 proton), 3.75-3.84 (m, 4H, —CH₂—) ppm. MS (neg. ion FAB): 1030 (M⁻), 590,438.

EXAMPLE 26

Rapamycin 42-ester with morpholine-4-carboxylic acid

A solution of 95 mg (1.1 mmole) morpholine in 1 mL dry dichloromethane was added to a stirred solution of 330 mg (0.31 mmole) rapamycin-42-(4-nitrophenyl)carbonate in 6 mL dichloromethane at −5° C. under nitrogen; stirring was continued 4.5 hours at −5° and 2 hours at 20°. The reaction mixture was partitioned between dichloromethane and water/brine; the organic portion was washed with brine and flash chromatographed through silica gel using methanol (1.0 to 1.6%) in dichloromethane, yielding 70 mg product as a white solid, mp 105°-115° C.

IR (KBr): 3450, 2950, 1710, 1650, 1250, and 993 cm⁻¹.

NMR (CDCl3, 400 MHz): δ3.64 (4H, 3-morpholine); 3.46 (t (J=4.9 Hz), 4H, 2-morpholine); 3.37 (s, 3H, OMe); 3.32 (s, 3H, OMe); 3.12 (s, 3H, OMe) ppm.

MS (neg ion FAB): 1026 (M−), 590.

EXAMPLE 27

Rapamycin 42-ester with 4-methylpiperazine-1-carboxylic acid

A solution of 95 mg (0.95 mmole) 1-methylpiperazine in 2 mL dichloromethane was added to a solution of 310 mg (0.29 mmole) rapamycin-42-(4-nitrophenyl)carbonate in 6 mL dichloromethane at 0° C. under nitrogen and stirred at 0° for 2 hours and at 20° for 2 hours. The reaction mixture was partitioned between dichloromethane and water/brine. The organic portion was washed with brine and flash chromatographed through silica gel using methanol (2.0 to 3.0%) in dichloromethane, yielding 120 mg product as a white solid, mp 108°-116° C.

IR (KBr): 3450, 2945, 1710, 1650, 1460, 1240, 1110, and 990 cm⁻¹.

NMR (CDCl3, 400 MHz): δ3.50 (broad, 4H, 2-piperazine); 3.39 (s, 3H, OMe); 3.33 (s, 3H, OMe); 3.14 (s, 3H, OMe); 2.36 (broad, 4H, 3-piperazine); 2.30 (s, 3H, NMe) ppm.

MS (neg ion FAB): 1039 (M−), 590.

EXAMPLE 28

Rapamycin 42-ester with piperazine-1-carboxylic acid

A solution of 190 mg (2.2 mmole) piperazine in 4 mL dichloromethane was added to a solution of 550 mg (0.51 mmole) rapamycin-42-(4-nitrophenyl)carbonate in 12 mL dichloromethane at 0° C. under nitrogen and stirred 45 minutes. Partitioning between dichloromethane and water/brine, washing with brine and flash chromatography through silica gel using 5% methanol in dichloromethane yielded 350 mg product as a pale yellow solid, mp 120°-131° C.

IR (KBr): 3460, 2950, 1705, 1650, 1460, 1245, and 990 cm⁻¹.

NMR (CDCl3, 400 MHz): δ4.8 (broad, 1H, NH); 3.46 (broad, 4H, 2piperazine); 3.39 (s, 3H, OMe); 3.33 (s, 3H, OMe); 3.14 (s, 3H, OMe); 2.83 (broad, 4H, 3-piperazine) ppm.

MS (neg ion FAB): 1025 (M−), 590.

What is claimed is:

1. A compound having the structure

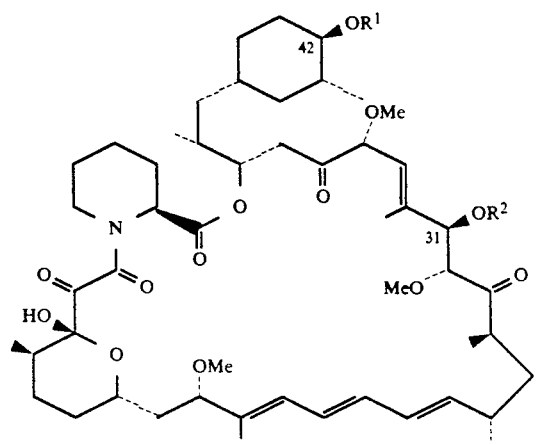

wherein
R¹ and R² are each, independently, hydrogen, or —CONH—[(CR³R⁴)ₘ(—A—(CR⁵R⁶)ₙ)ₚ]_q—B;
R³, R⁴, R⁵, and, R⁶ are each, independently, alkyl of 1-6 carbon atoms, phenylalkyl of 7-10 carbon atoms, piperazinylalkyl of 7-10 carbon atoms, piperidinylalkyl of 7-10 carbon atoms, pyridylalkyl of 7-10 carbon atoms, cycloalkyl of 3-8 carbon atoms, —OR⁷, —SR⁷, halogen, —CN, —NO₂, —CF₃, —COR₇, —CONH₂, —SO₂R₇, —OSO₃R⁷, —NR⁷R⁸, —NHCOR⁷, —NHSO₂R⁸, or Ar;
B is hydroxy, —SR⁷, —CN, —COR₇, —CONH₂, —OSO₃R⁷, —NR⁷R⁸, —NHCOR⁷, —NHSO₂R⁸, or Ar;
A is —CH₂—, —NR⁷—, —O—, —S—, —PR⁷—, or —P(O)(R⁷)—;
R⁷ and R⁸ are each, independently, hydrogen, alkyl of 1-6 carbon atoms, phenylalkyl of 7-10 carbon atoms, piperazinylalkyl of 7-10 carbon atoms, piperidinylalkyl of 7-10 carbon atoms, pyridylalkyl of 7-10 carbon atoms, or Ar;
Ar is naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri- substituted with a group selected from alkyl of 1-6 carbon atoms, phenylalkyl of 7-10 carbon atoms, piperazinylalkyl of 7-10 carbon atoms, piperidinylalkyl of 7-10 carbon atoms, pyridylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;
with the proviso that R¹ and R² are not both hydrogen;
m=0-6;
n=0-6;

p=0-1;
q=0-1;
or a pharmaceutically acceptable salt thereof.

2. The compound according to claim 1 wherein $R^2$ is hydrogen.

3. The compound according to claim 1, wherein p=0 and B is Ar.

4. The compound according to claim 3 wherein $R^2$ is hydrogen.

5. The compound according to claim 1, wherein m=2, n=0, p=1, q=1, and A is —O— or —$NR^7$.

6. The compound according to claim 1 which is rapamycin 42-ester with 2-hydroxyethyl carbamic acid or a pharmaceutically acceptable salt thereof.

7. The compound according to claim 1 which is rapamycin 42-ester with 2-(dimethylamino)ethyl carbamic acid or a pharmaceutically acceptable salt thereof.

8. The compound according to claim 1 which is rapamycin 42-ester with aminocarbamic acid or a pharmaceutically acceptable salt thereof.

9. The compound according to claim 1 which is rapamycin 42-ester with hydroxycarbamic acid or a pharmaceutically acceptable salt thereof.

10. The compound according to claim 1 which is rapamycin 42-ester with 2-(pyridin-2-yl)-ethyl carbamic acid or a pharmaceutically acceptable salt thereof.

11. The compound according to claim 1 which is rapamycin 42-ester with 2-(pyridin-2-yl)-ethyl carbamic acid hydrochloride salt.

12. The compound according to claim 1 which is rapamycin 42-ester with 2-(pyridin-2-yl)-ethyl carbamic acid methanesulfonate salt.

13. The compound according to claim 1 which is rapamycin 42-ester with 2-(pyridin-2-yl)-ethyl carbamic acid maleate salt.

14. The compound according to claim 1 which is rapamycin 42-ester with 2-pyridinylmethyl carbamic acid or a pharmaceutically acceptable salt thereof.

15. The compound according to claim 1 which is rapamycin 42-ester with 2-pyridinylmethyl carbamic acid hydrochloride salt.

16. The compound according to claim 1 which is rapamycin 42-ester with 3-pyridinylmethyl carbamic acid or a pharmaceutically acceptable salt thereof.

17. The compound according to claim 1 which is rapamycin 42-ester with 3-pyridinylmethyl carbamic acid hydrochloride salt.

18. The compound according to claim 1 which is rapamycin 42-ester with 4-pyridinylmethyl carbamic acid or a pharmaceutically acceptable salt thereof.

19. The compound according to claim 1 which is rapamycin 42-ester with 4-pyridinylmethyl carbamic acid hydrochloride salt.

20. The compound according to claim 1 which is rapamycin 42-ester with 2-furylmethyl carbamic acid or a pharmaceutically acceptable salt thereof.

21. The compound according to claim 1 which is rapamycin 42-ester with 2-pyridinylmethyl carbamic acid methanesulfonate salt.

22. The compound according to claim 1 which is rapamycin 42-ester with 4-hydroxybutyl carbamic acid or a pharmaceutically acceptable salt thereof.

23. The compound according to claim 1 which is rapamycin 42-ester with (S)-1-methyl-2-hydroxyethyl carbamic acid or a pharmaceutically acceptable salt thereof.

24. The compound according to claim 1 which is rapamycin 42-ester with (R)-1-methyl-2-hydroxyethyl carbamic acid or a pharmaceutically acceptable salt thereof.

25. The compound according to claim 1 which is rapamycin 42-ester with 2-(2-aminoethoxy)ethyl carbamic acid or a pharmaceutically acceptable salt thereof.

26. The compound according to claim 1 which is rapamycin 42-ester with dihydroxyispropyl carbamic acid or a pharmaceutically acceptable salt thereof.

27. The compound according to claim 1 which is rapamycin 42-ester with [3-[bis(2-hydroxyethyl)amino]-propyl]carbamic acid or a pharmaceutically acceptable salt thereof.

28. A method of inducing immunosuppression by administering an immunosuppressive amount of a compound having the structure wherein
$R^1$ and $R^2$ are each, independently, hydrogen, or —CONH—[$(CR^3R^4)_m$(—A—$(CR^5R^6)_n)_p]_q$—B;
$R^3$, $R^4$, $R^5$, and, $R^6$ are each, independently, hydrogen, alkyl of 1–6 carbon atoms, phenylalkyl of 7–10 carbon atoms, piperazinylalkyl of 7–10 carbon atoms, piperidinylalkyl of 7–10 carbon atoms, pyridylalkyl of 7–10 carbon atoms, cycloalkyl of 3–8 carbon atoms, —$OR^7$, —$SR^7$, halogen, —CN, —$NO_2$, —$CF_3$, —$COR_7$, —$CONH_2$, —$SO_2R_7$, —$OSO_3R^7$, —$NR^7R^8$, —$NHCOR^7$, —$NHSO_2R^8$, or Ar;

B is hydroxy, —$SR^7$, —CN, —$COR_7$, —$CONH_2$, —$OSO_3R^7$, —$NR^7R^8$, —$NHCOR^7$, —$NHSO_2R^8$, or Ar;

A is —$CH_2$—, —$NR^7$—, —O—, —S—, —$PR^7$—, or —P(O)($R^7$)—;

$R^7$ and $R^8$ are each, independently, hydrogen, alkyl of 1–6 carbon atoms, phenylalkyl of 7–10 carbon atoms, piperazinylalkyl of 7–10 carbon atoms, piperidinylalkyl of 7–10 carbon atoms, pyridylalkyl of 7–10 carbon atoms, or Ar;

Ar is naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri- substituted with a group selected from alkyl of 1–6 carbon atoms, phenylalkyl of 7–10 carbon atoms, piperazinylalkyl of 7–10 carbon atoms, piperidinylalkyl of 7–10 carbon atoms, pyridylalkyl of 7–10 carbon atoms, alkoxy of 1–6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H;

with the proviso that R$^1$ and R$^2$ are not both hydrogen;

m=0-6;
n=0-6;
p=0-1;
q=0-1;

or a pharmaceutically acceptable salt thereof.

29. The method according to claim 28 wherein the induced immunosuppression is used to prevent or treat transplantation rejection or host versus graft disease.

30. The method according to claim 28 wherein the induced immunosuppression is used to treat autoimmune diseases, diseases of inflammation, or hyperproliferative vascular disorders.

31. A pharmaceutical composition for use as an immunosuppressive agent comprising an immunosuppressive amount of a compound of the structure

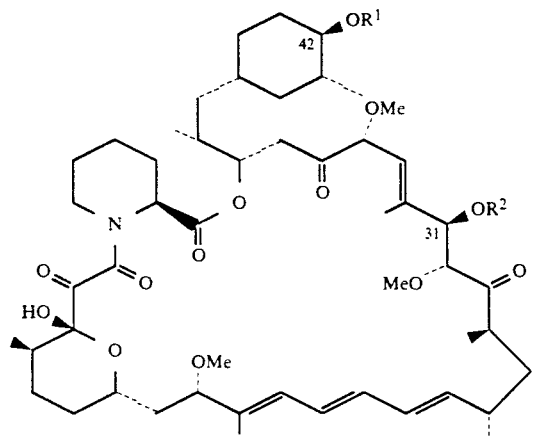

wherein
R$^1$ and R$^2$ are each, independently, hydrogen, or —CONH—[(CR$^3$R$^4$)$_m$(—A—(CR$^5$R$^6$)$_n$)$_p$]$_q$—B;

R$^3$, R$^4$, R$^5$, and, R$^6$ are each, independently, hydrogen, alkyl of 1-6 carbon atoms, phenylalkyl of 7-10 carbon atoms, piperazinylalkyl of 7-10 carbon atoms, piperidinylalkyl of 7-10 carbon atoms, pyridylalkyl of 7-10 carbon atoms, cycloalkyl of 3-8 carbon atoms, —OR$^7$, —SR$^7$, halogen, —CN, —NO$_2$, —CF$_3$, —COR$_7$, —CONH$_2$, —SO$_2$R$_7$, —OSO$_3$R$^7$, —NR$^7$R$^8$, —NHCOR$^7$, —NHSO$_2$R$^8$, or Ar;

B is hydroxy, —SR$^7$, —CN, —COR$_7$, —CONH$_2$, —OSO$_3$R$^7$, —NR$^7$R$^8$, —NHCOR$^7$, —NHSO$_2$R$^8$, or Ar;

A is —CH$_2$—, —NR$^7$—, —O—, —S—, —PR$^7$—, or —P(O)(R$^7$)—;

R$^7$ and R$^8$ are each, independently, hydrogen, alkyl of 1-6 carbon atoms, phenylalkyl of 7-10 carbon atoms piperazinylalkyl of 7-10 carbon atoms, piperidinylalkyl of 7-10 carbon atoms, pyridylalkyl of 7-10 carbon atoms, or Ar;

Ar is naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri- substituted with a group selected from alkyl of 1-6 carbon atoms, phenylalkyl of 7-10 carbon atoms, piperazinylalkyl of 7-10 carbon atoms, piperidinylalkyl of 7-10 carbon atoms, pyridylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H;

with the proviso that R$^1$ and R$^2$ are not both hydrogen;

m=0-6;
n=0-6;
p=0-1;
q=0-1;

or a pharmaceutically acceptable salt thereof, and a pharmaceutical carrier.

32. A compound of the structure

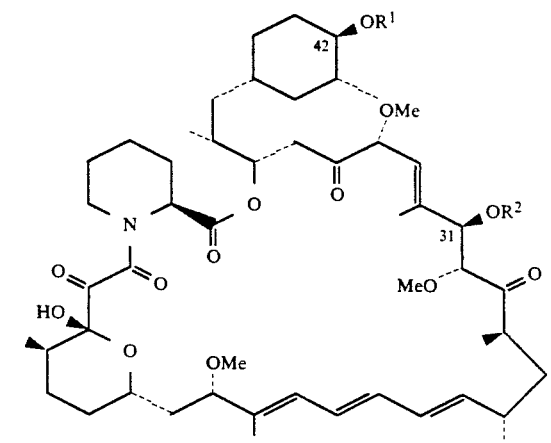

wherein
R$^1$ and R$^2$ are each, independently, hydrogen, or —CONH—(CR$^3$R$^4$)$_m$—B;

B is pyridyl which may be optionally mono-, di-, or tri-substituted with a group selected from alkyl of 1-6 carbon atoms, phenylalkyl of 7-10 carbon atoms, piperazinylalkyl of 7-10 carbon atoms, piperidinylalkyl of 7-10 carbon atoms, pyridylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H;

R$^3$ and R$^4$ are each, independently, hydrogen or alkyl of 1-6 carbon atoms; and m=0-6;

with the proviso that R$^1$ and R$^2$ not both hydrogen, or a pharmaceutically acceptable salt thereof.

33. The compound of claim 32 wherein R$^2$ is hydrogen.

* * * * *